United States Patent [19]
Heintz

[11] Patent Number: 5,655,258
[45] Date of Patent: Aug. 12, 1997

[54] DEVICE FOR ASPIRATING FLUIDS FROM HOSPITAL OPERATING ROOM FLOOR

[76] Inventor: J. Aaron Heintz, 26 Primrose Dr., Richboro, Pa. 18954

[21] Appl. No.: 615,569

[22] Filed: Mar. 12, 1996

[51] Int. Cl.⁶ ..................................................... A47L 9/02
[52] U.S. Cl. ................................. 15/415.1; 604/317
[58] Field of Search ........................ 15/322, 415.1, 15/417, 420; 604/313, 317, 902

[56] References Cited

U.S. PATENT DOCUMENTS

| | | | |
|---|---|---|---|
| 1,054,052 | 2/1913 | Stewart | 15/415.1 |
| 2,816,664 | 12/1957 | Haynes . | |
| 2,966,694 | 1/1961 | Brown . | |
| 3,520,300 | 7/1970 | Flower | 604/902 |
| 3,605,171 | 9/1971 | Candor et al. . | |
| 4,041,569 | 8/1977 | Petersen . | |
| 4,156,948 | 6/1979 | Chauvier et al. . | |
| 4,279,057 | 7/1981 | Restivo | 15/415.1 |
| 4,679,590 | 7/1987 | Hergenroeder . | |
| 4,729,146 | 3/1988 | Barr | 15/415.1 |
| 4,729,404 | 3/1988 | Hergenroeder . | |
| 5,014,389 | 5/1991 | Ogilvie et al. . | |
| 5,032,184 | 7/1991 | Ogilvie . | |
| 5,267,370 | 12/1993 | Worwag . | |
| 5,295,982 | 3/1994 | Schatz | 604/313 |
| 5,437,651 | 8/1995 | Todd et al. | 15/420 |

FOREIGN PATENT DOCUMENTS

| | | | |
|---|---|---|---|
| 875054 | 7/1971 | Canada | 15/420 |

*Primary Examiner*—David Scherbel
*Assistant Examiner*—Terrence Till
*Attorney, Agent, or Firm*—Caesar, Rivise, Bernstein, Cohen & Pokotilow, Ltd.

[57] ABSTRACT

A suction device for removing liquids from a surface such as a floor. The device includes an air chamber formed from a top and a bottom plate, each of the plates having a respective top and bottom surface. The air chamber is in fluid communication with a fitting adjacent thereto. The bottom plate includes a plurality of holes therethrough. The bottom surface of the bottom plate additionally includes fabric adjacent thereto and feet to hold the bottom plate of the device up off the floor to enable fluid to be suctioned through the bottom plate holes and into the chamber via a conventional source of suction.

8 Claims, 2 Drawing Sheets

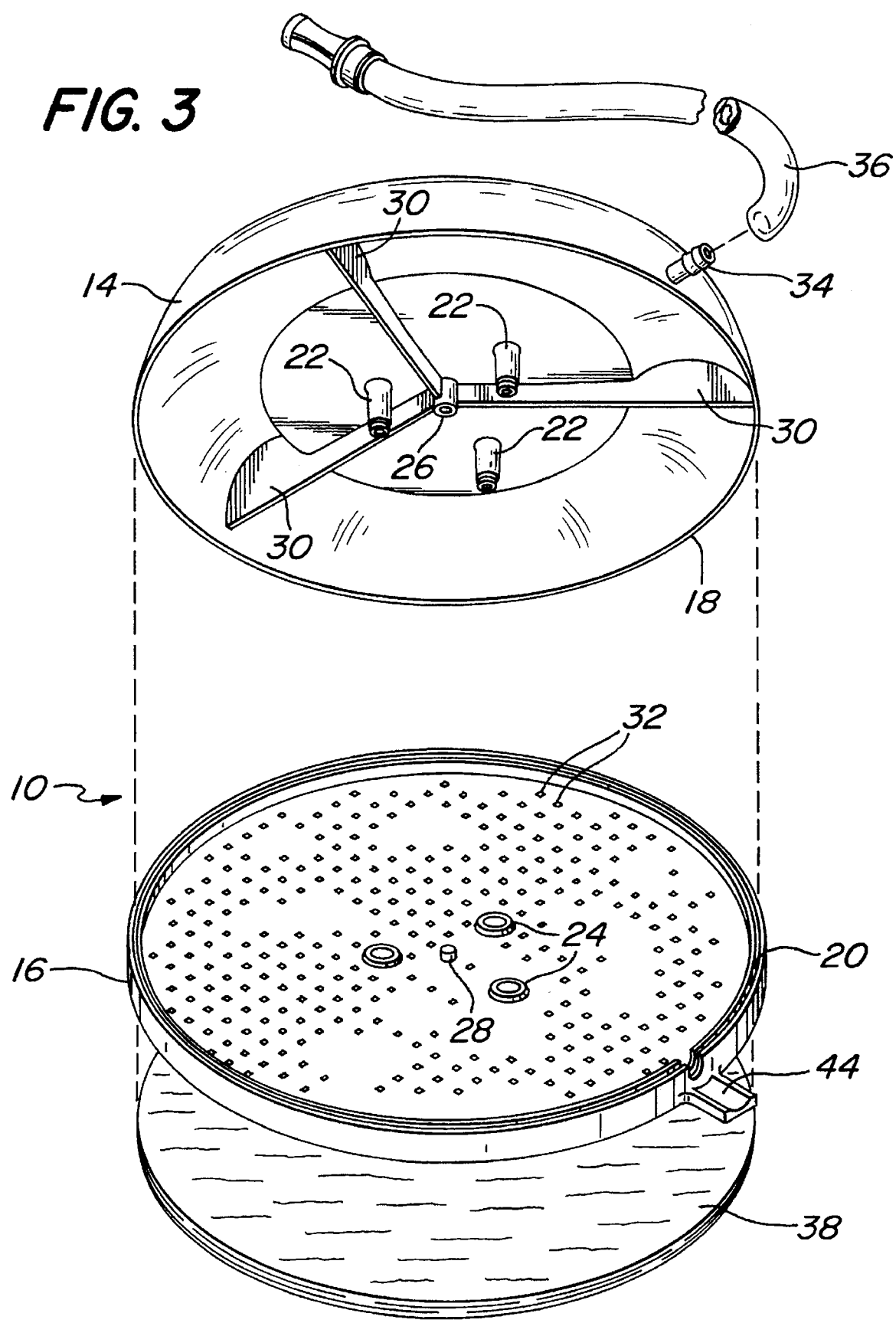

DEVICE FOR ASPIRATING FLUIDS FROM HOSPITAL OPERATING ROOM FLOOR

BACKGROUND OF THE INVENTION

The present invention relates to an apparatus to remove fluid that drains or spills onto the floor during surgery.

During surgery waste fluids of various types find their way to the floor of the operating room. For example, during arthroscopic surgery sterile fluid (e.g., saline) is supplied to the surgical site. This fluid, if permitted to drain uncontrolled to the floor, presents an additional hazard.

A prior art approach toward solving this problem is disclosed in U.S. Pat. Nos. 4,679,590 and 4,729,404. These patents disclose a rubber mat to be placed beneath a surgical site in sealed engagement with the floor. The top surface of the mat is configured as multiple inverted pyramidal elements configured to collect fluid and direct it to a drain hole on the bottom side of the mat. The bottom side of the mat is provided with flow channels that become sealed to the floor and converge to a common suction port adapted for connection to a source of suction that is commonly available at wall-mounted suction ports in surgical operating rooms. The suction delivers the recovered fluid to a canister for disposal.

The suction mat arrangement described above appear to not be able to drain the rather significant amount of fluid that falls to the floor beyond the mat periphery. During arthroscopic surgery the sterile fluid delivered to the surgical side is often delivered at relatively high pressures, thereby making it difficult, if not impossible, for surgical personnel to direct the fluid so that, after flowing from the surgical site, it falls on the suction mat.

There are commercially available vacuum cleaners with movable suction heads adapted to draw liquid from floors toward a waste collection chamber. These devices, however, are not suitable for surgical environments for a number of reasons, not the least of which is the fact that the vacuum cleaner suction head must be manipulated by hand in order to be positioned at various spillage locations on the floor. Since the hands of operating room personnel are otherwise occupied during a surgical procedure, the use of a commercial vacuum cleaner would require additional personnel, thereby adding to the already high cost of surgery. Moreover, commercially available vacuum cleaners have built-in vacuum sources that are extremely noisy, thereby rendering communication between the surgeon and nurses difficult at best. It would be far more desirable to use a low level suction source (e.g., on the order of 300 millimeters of mercury below atmosphere pressure) such as is commonly available at a wall port in operating rooms; however, suction heads employed with commercial vacuum cleaners are incapable of operating at such low pressures.

Finally, the fluids that spill onto the floor during a surgical procedure are likely to be or become contaminated. Commercially available vacuum cleaner heads for liquids are not designed to be disposable after use and, accordingly, would become contaminated and present a health hazard.

In U.S. Pat. Nos. 5,032,184 and 5,014,389 (Ogilvie et al.) is disclosed a method and apparatus having a suction head for use in removing waste fluids from surgical operating room floors. The apparatus has a planar, low-friction bottom surface adapted to slide along the floor in response to translational forces applied by the foot of a surgeon, nurse or other surgery personnel. Flow channels recessed in the bottom surface extend from the periphery of the suction head to the mouth of a common suction port adapted for connection by flexible tubing to a waste fluid collection container or canister. The canister is also connected by means of a hose to a wall mounted suction port providing a negative low pressure on the order of 300 millimeters of mercury below atmospheric pressure. In the preferred embodiment, the suction head is a thin one-piece molded plate, preferably of resilient plastic material having a heat distortion temperature less than 270° F., so as to be sufficiently inexpensive to be discarded after each surgical procedure. The common suction port is defined as a tubular hose fitting extending upwardly from the top surface of the plate. Multiple support ribs extend along the top surface from the hose fitting to the suction head periphery in juxtaposition with respective flow channels to reinforce the flow channels against collapse and flow blockage.

Unlike the Ogilvie device, in the present invention, the barbed fitting exists the device at the side, so as to minimize a potential trip hazard in a surgical environmental which is typically encumbered with several fluid, electrical, and other lines.

Other patents showing suction devices and/or floor drainers include U.S. Pat. No. 2,966,694 (C. L. Brown, Jr.), U.S. Pat. No. 2,816,664 (R. H. Haynes), U.S. Pat. No. 3,605,171 (R. R. Candor et al.), U.S. Pat. No. 4,041,569 (Petersen), U.S. Pat. No. 4,156,948 (Chauvier et al.) and U.S. Pat. No. 5,267,370 (Worwag).

BRIEF SUMMARY OF THE INVENTION

These and other objects of this invention are achieved by providing a suction device for removing liquids from a surface such as a floor. The device includes an air chamber formed from a top and a bottom plate, each of the plates having a respective top and bottom surface. The air chamber is in fluid communication with a fitting adjacent thereto. The bottom plate includes a plurality of holes therethrough. The bottom surface of the bottom plate additionally includes fabric adjacent thereto and feet to hold the bottom plate of the device up off the floor to enable fluid to be suctioned through the bottom plate holes and into the chamber via a conventional source of suction.

BRIEF DESCRIPTION OF THE DRAWINGS

Other objects and many attendant features of this invention will become readily appreciated as the same becomes better understood by reference to the following detailed description when considered in connection with the accompanying drawings wherein:

FIG. 3 is an exploded view of the device of FIG. 1.

DETAILED DESCRIPTION OF THE INVENTION

Figure 1:
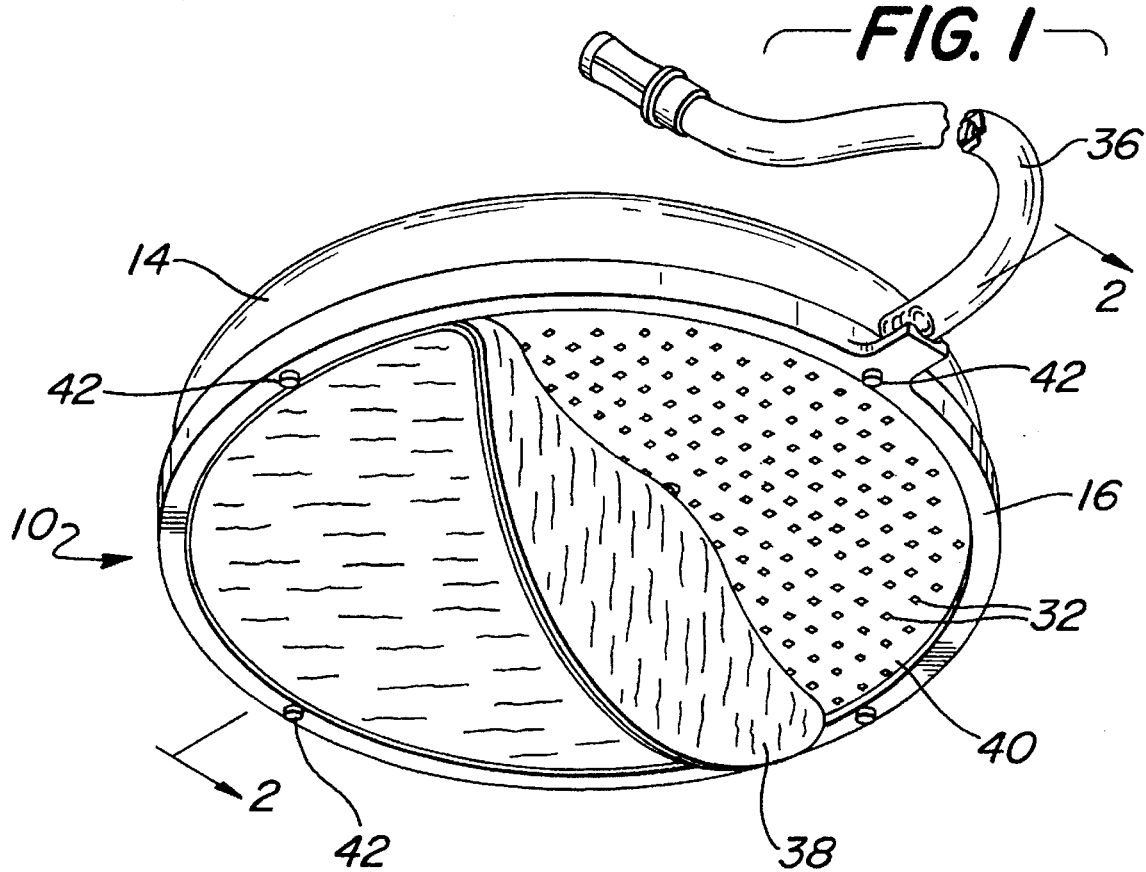
FIG. 1 is a bottom view of the device of the present invention showing the fabric of the bottom plate partially removed.

Referring now to various figures of the drawings where like reference numerals refer to like parts, there is shown at 10 in FIG. 1, a device constructed in accordance with this invention.

Figure 2:
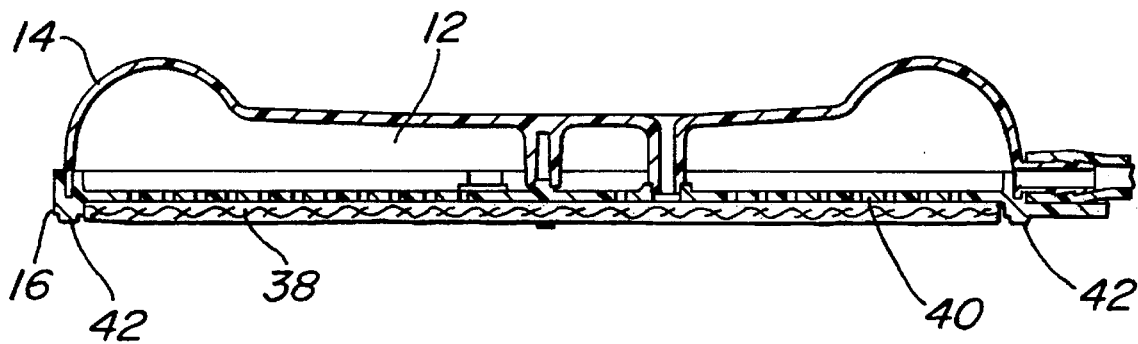
FIG. 2 is a cross-sectional view of the device of FIG. 1, taken along line 2—2 of FIG. 1.

The device 10 of the present invention consists of an air chamber 12 shown in FIG. 2, approximately 8 to 10 inches in diameter and ¾ to 1½ inches thick. The air chamber 12 is shown in a generally circular configuration, although any suitable shape may be utilized. The chamber 12 has top and bottom sections. In the preferred embodiment the chamber 12 is formed from a top plate 14 and a bottom 16 plate, which can be either bonded or snapped together. However, integral construction is not excluded.

In the preferred embodiment both the top and bottom plates are made of ABS plastic.

As shown in FIG. 3, the top plate 14 has a cooperative circumferential edge 18 for example, which may be secured in a tapered rim, forming a self sealing air lock (tapered fit) into the cooperative mating edge 20 of bottom plate 16. In order to aid in the tapered fit of the top plate 14 to the bottom plate 16, the top plate 14 includes depending members 22 which cooperatively fit within respective recesses 24 located in bottom plate 16. The top plate 14 may also include receptacle 26 which is secured (e.g., ultrasonic welded, glued, etc.) to cooperative member 28 of bottom plate 16 shown in FIG. 3. The top plate 14 may further include radial stiffening ribs 30 as shown in FIG. 3 and may still further have one or more depressions in its top surface or a single large depression in its center to collect liquid or provide a place to permit receipt of the tip of a shoe of a person to move the device.

As shown in FIGS. 1 and 3, the bottom plate 16 also has a disc with a plurality of small holes 32, typically 0.40 to 0.090 inches in diameter, which communicate from the bottom (fluid source) of the device 10 to the air chamber 12 inside the device 10. The air chamber 12, in turn, communicates with a barbed fitting 34 and the suction line 36 which is connected to a conventional vacuum source (not shown). The plurality of small holes 32 permit the suction and/or transmission of fluid (not shown) therethrough.

As shown in FIGS. 1 and 2, a disk 38 of preferably absorbent, non-woven fabric is applied to the bottom 40 of the bottom plate 16. The fabric is typically constructed of a polypropylene/cellulose blend for maximum absorbency. The fabric acts additionally as a sound baffling mechanism to reduce the annoying distraction of operating room noise.

As shown in FIGS. 1 and 2, the bottom plate 16 also has several small (0.040 to 0.90 inch high) "feet" 42 which hold the device 10 up off the floor. The purpose for this is twofold. The feet 42 hold the suction holes 32 up off the floor so as to avoid having the device 10 sucked down onto the floor and rendered immovable. Secondly, the feet 42 allow the device 10 to be kicked by operating room personnel into a puddle without significant splashing of surrounding fluid (not shown). The device 10 will skim across the top of the puddle with minimal disruption (splashing) to the fluid, providing increased safety to the clinicians. Furthermore, the height of a puddle of fluid on a concrete, linoleum, or similar slick construction materials is a relatively constant one, dictated by the surface tension, density, and viscosity of the water. The height of the feet 42 is optimized to take best advantage of this known height (approximately 0.5 to 0.9 times the height of a typical puddle).

As shown in FIG. 3, the barbed fitting 34 is slightly recessed into the bottom plate 16 to form a lower reservoir 44 for the collection of fluids. In a preferred form (not shown) the barbed fitting 34 is integral with the top plate where there is no lower reservoir 44. Thus, there is only a planar support member without a reservoir. While the conventional vacuum source (not shown) does provide a dynamic pressure to pull the fluids into the suction line 36, this geometry will assist the flow of fluid through the force of gravity.

The device 10 of the present invention facilitates aspiration of fluids from a surgical operating room. The device 10 easily slides across the floor upon being kicked, so as to be moved to puddles of spilled fluids. While the device 10 could be used in almost any surgical procedure, it is most applicable for those procedures which use a large amount of irrigation solution (typically saline or other water-based solutions). These procedures, such as arthroscopy (joint surgery) and cystoscopy (surgery of the urinary tract) and hysteroscopy (surgery of the uterus) can use up to twenty liters of fluid, several liters of which can typically be spilled on the floor.

The device of the present invention can be attached to the built-in suction source present in nearly every operating room. An intermediate canister (not shown) is typically employed as a fluid trap to avoid contamination of the vacuum lines and pump.

The present invention may be supplied with pre-attached tubing for convenience, but could also be supplied without tubing.

In an alternate form of the invention, the bottom plate 16 of air chamber 12 may be finely porous, with more and smaller holes 32, such that the woven fabric is dispensed with. Also, the holes can drain through the top section or even that there is no disc with small holes in the interior of the chamber 12.

Without further elaboration the foregoing will so fully illustrate my invention that others may, by applying current or future knowledge, adapt the same for use under various conditions of service.

I claim:

1. A floor engaging moveable suction device for removing liquids from a floor, the device having an outer surface, defining means to permit the device to be kicked to different locations on the floor, the device comprising an air chamber in fluid connection with a vacuum source, and means comprising floor contacting feet extending away from the air chamber to hold the device up and away from contact with the floor and a suction line being secured to the air chamber.

2. The device of claim 1 wherein the device is comprised of a top and bottom plate which are formed of plastic.

3. The device of claim 1 wherein the chamber is defined by a top plate and a bottom plate secured together.

4. The device of claim 3 wherein the bottom plate has a plurality of small holes in fluid communication with the air chamber.

5. The device of claim 4 wherein the holes have a diameter of 0.090".

6. The device of claim 4 further including a porous fabric secured against said bottom plate and facing toward said floor.

7. The device of claim 6 wherein the porous fabric is a polypropylene/cellulose blend.

8. The device of claim 1 wherein the feet are approximately 0.040" high.

* * * * *